(12) United States Patent
Deitch

(10) Patent No.: US 9,078,729 B2
(45) Date of Patent: Jul. 14, 2015

(54) BODY IMPLANTABLE FABRIC

(75) Inventor: Sarah J. Deitch, Stillwater, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/894,152

(22) Filed: Sep. 30, 2010

(65) Prior Publication Data

US 2011/0077457 A1     Mar. 31, 2011

(51) Int. Cl.
     *A61B 17/08*     (2006.01)
     *A61B 17/42*     (2006.01)
     *A61F 2/02*     (2006.01)
     *A61F 2/00*     (2006.01)

(52) U.S. Cl.
     CPC ............ *A61F 2/0045* (2013.01); *A61F 2/0063* (2013.01); *A61F 2002/0086* (2013.01); *A61F 2250/0031* (2013.01)

(58) Field of Classification Search
USPC ............... 606/13–15, 151–156, 216; 600/37; 623/23.72, 23.75
IPC ....................................................... A61B 17/08
See application file for complete search history.

(56) References Cited

U.S. PATENT DOCUMENTS

| | | | | |
|---|---|---|---|---|
| 5,368,602 A | * | 11/1994 | de la Torre | 606/151 |
| 5,554,808 A | | 9/1996 | Chiao | |
| 5,695,525 A | * | 12/1997 | Mulhauser et al. | 606/151 |
| 2003/0078602 A1 | * | 4/2003 | Rousseau | 606/151 |
| 2005/0228408 A1 | | 10/2005 | Fricke et al. | |
| 2005/0267325 A1 | * | 12/2005 | Bouchier et al. | 600/37 |
| 2006/0025785 A1 | | 2/2006 | Cully et al. | |
| 2006/0282105 A1 | * | 12/2006 | Ford et al. | 606/151 |
| 2008/0065229 A1 | | 3/2008 | Adams | |
| 2008/0234543 A1 | | 9/2008 | Goldwasser | |
| 2009/0082792 A1 | * | 3/2009 | Koyfman et al. | 606/151 |
| 2009/0171377 A1 | | 7/2009 | Intoccia et al. | |
| 2009/0270999 A1 | * | 10/2009 | Brown | 623/23.72 |

FOREIGN PATENT DOCUMENTS

| | | |
|---|---|---|
| CA | 2357020 | 1/2001 |
| CN | 101534746 | 9/2009 |
| WO | 0007520 | 2/2000 |
| WO | 2006071023 | 7/2006 |
| WO | 2009/005714 A2 | 1/2009 |

OTHER PUBLICATIONS

International search report and written opinion from the related International application No. PCT/DK2010/050248, dated Dec. 2, 2010.
Office Action mailed on Jun. 13, 2013 in U.S. Appl. No. 12/571,444.
Analysis of failures and strategy of patient's treatment dated Sep. 29, 2014—USA, Pennsylvania, 1996, p. 11 from 19 Article in Russian and translation into English of relevant part attached.

* cited by examiner

*Primary Examiner* — Yashita Sharma
(74) *Attorney, Agent, or Firm* — Coloplast Corp., Coloplast A/S; Nick Baumann

(57) ABSTRACT

An implantable fabric includes a bio-inert portion having a first surface and an opposing second surface, with each of the first and second surfaces configured for tissue ingrowth and a bio-absorbable portion attached to the bio-inert portion in a manner that substantially prevents wrinkles on each of the first and second surfaces of the bio-inert portion.

14 Claims, 6 Drawing Sheets

BODY IMPLANTABLE FABRIC

BACKGROUND

Pelvic organ prolapse refers to a disorder related to the dropping down (prolapse) of the bladder, rectum, or uterus caused by weakness or injury to ligaments, connective tissue, or muscles of the pelvis. The various forms of pelvic organ prolapse are categorized according to the organ affected. For example, a rectocele develops when the rectum drops down and protrudes into the back wall of the vagina. An enterocele develops when the small intestine and the lining of the abdomen bulge downward between the uterus and the rectum or, if the uterus has been removed, between the bladder and the rectum. A cystocele develops when the bladder drops down and protrudes into the front wall of the vagina. In prolapse of uterus, the uterus drops down into the vagina.

Surgical procedures have been developed to repair pelvic organ prolapse, for example through the use of support materials implanted within the pelvis to strengthen the ligaments, connective tissue, or muscles of the pelvis. While the surgical procedures are generally effective, the patient can at times experience dysparunea (pain or the sensation of pain during vaginal intercourse), which is thought to be related to the undesired wrinkling or gathering of the implanted support material in the pelvic region.

SUMMARY

One aspect provides an implantable fabric including a bio-inert portion having a first surface and an opposing second surface, with each of the first and second surfaces configured for tissue ingrowth and a bio-absorbable portion attached to the bio-inert portion in a manner that substantially prevents wrinkles on each of the first and second surfaces of the bio-inert portion.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
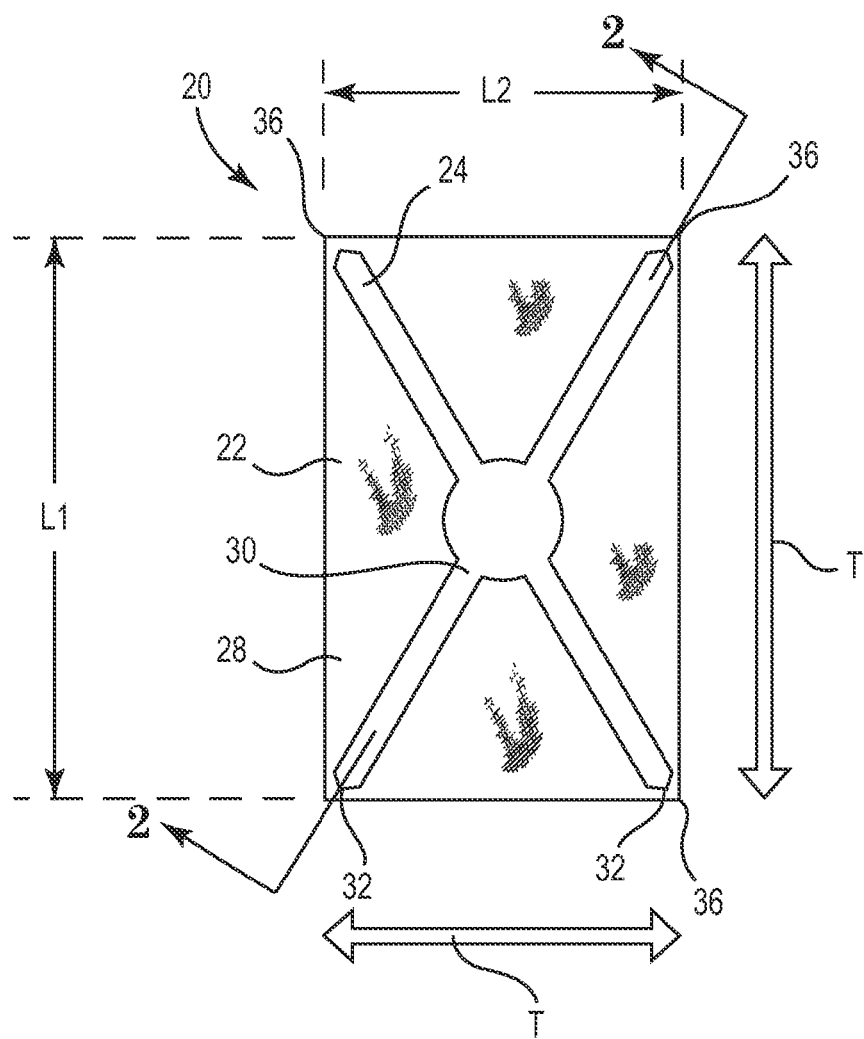
FIG. 1 is a top view of an implantable fabric including a bio-inert portion reinforced by a bio-absorbable portion according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

It is desirable to implant materials to support to the ligaments, connective tissue, or muscles of the pelvis in treating pelvic organ prolapse. However, some implanted materials have the potential to wrinkle or gather into folds, which is thought to undesirably contribute to dysparunea. Some implanted materials are configured to "self expand" after implantation, and the expansion has the potential to develop undesirable wrinkles/folds. Still other implanted materials have a "tissue adhesion barrier" side that prevents tissue ingrowth into both major surfaces of the implant.

Embodiments provide an implantable fabric suited for repair of pelvic organ prolapse, where the fabric is configured to allow tissue ingrowth through all of the major surfaces in a manner that ensures the implanted fabric will be strong enough to support the ligaments, connective tissue, or muscles of the pelvis in treating pelvic organ prolapse. The implantable fabric described herein is provided in a format that is compatible with conventional surgical implantation techniques and also prevents wrinkles on the implanted fabric, which helps to reduce or eliminate the undesirable effects of dysparunea.

Embodiments provide an implantable fabric suited for repair of pelvic organ prolapse that includes a bio-inert portion supported by a bio-absorbable portion. The bio-absorbable portion prevents wrinkles in the bio-inert portion as the bio-inert portion heals into place after implantation into the patient. Eventually, the bio-absorbable portion is bio-absorbed into the patient leaving behind a substantially wrinkle free bio-inert portion implanted within a patient to strengthen the ligaments, connective tissue, or muscles of the pelvis. The bio-inert portion is configured to allow tissue to grow through the top surface and the bottom surface of the bio-inert portion to effectively "anchor" the bio-inert portion within a patient.

Bio-inert means that the material is stable when implanted in an animal body.

Bio-absorbable means that the material will degrade or breakdown when implanted in an animal body. Bio-absorbable includes the disintegration of body implanted material, and the disintegration of body implanted material followed by the disintegrated material being absorbed into the body.

A wrinkle in the implantable fabric is an undulation in the fabric (e.g., a wavy fabric), where the undulation has more than one peak or more than one valley or where the fabric has portions that overlap. One particularly undesirable wrinkle is where the fabric has areas that overlap. Embodiments provide a fabric having bio-absorbable portion attached to at least one of the first and second surfaces of a bio-inert portion to support both of the first and second surfaces in a manner that substantially prevents the formation of a wrinkle on the surfaces after body implantation of the fabric.

Figure 2:
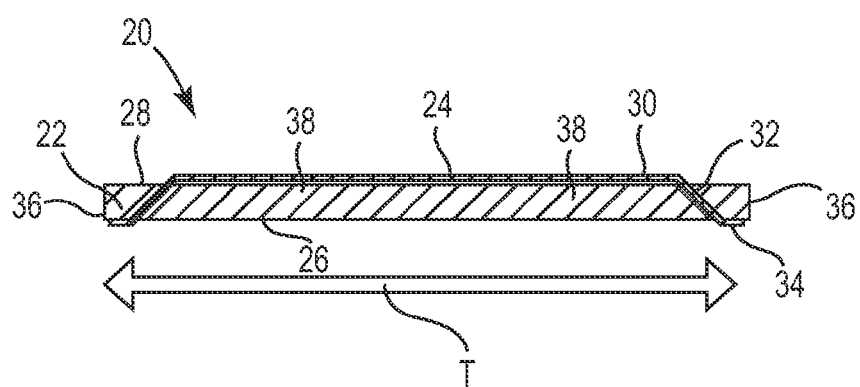
FIG. 2 is a cross-sectional view of the implantable fabric illustrated in FIG. 1.

FIG. 1 is a top view and FIG. 2 is a cross-sectional view of one embodiment of an implantable fabric 20 suitable for use in the treatment of pelvic organ prolapse. In one embodiment, fabric 20 includes a bio-inert portion 22 that is reinforced by a bio-absorbable portion 24. For example, the bio-inert portion 22 includes a first major surface 26 (a bottom surface) opposite a second major surface 28 (a top surface) and the bio-absorbable portion 24 is mechanically attached to the bio-inert portion 22 to hold the bio-inert portion 22 under tension T in a manner that prevents wrinkles on the surfaces 26, 28.

In one embodiment, the bio-absorbable portion 24 prevents wrinkles along at least one major direction of the bio-inert portion 22. For example, in one embodiment the bio-absorbable portion 24 prevents wrinkles in the longitudinal direction by separating ends of the bio-inert portion 22, or the bio-absorbable portion 24 prevents wrinkles in the lateral direction by separating sides of the bio-inert portion 22. In one embodiment, the bio-absorbable portion 24 prevents wrinkles in both the longitudinal and lateral directions of the bio-inert portion 22.

In one embodiment, the bio-absorbable portion 24 includes a body 30, a flange 32 extending from the body 30, and a prong 34 extending from the flange 32 that is configured to mechanically engage with the bio-inert portion 22. In this embodiment, the bio-absorbable portion 24 is provided as a separate film that is fabricated to have a stiffness that is greater than a stiffness of the bio-inert portion 22. The flanges 32 and the prongs 34 combine to hold corners 36 of the fabric 20 apart under tension from one another when the bio-absorbable portion 24 is coupled to the bio-inert portion 22. Thus, the bio-absorbable portion 24 provides an extension member 24 that is mechanically coupled to one of the opposed major surfaces 26, 28 of the bio-inert portion 22.

The bio-inert portion 22 is selected to be bio-compatible with implantation into a human body and is configured to allow tissue ingrowth throughout its structure to anchor the bio-inert portion 22 in the body after implantation and healing. Suitable bio-inert portions 22 include autograft material (the patient's own tissue), allograft material (tissue from a cadaver), xenograft material (tissue from another species), or synthetic materials such as woven fabrics, meshes, nonwoven fabrics, meshes, fibrillated fibers, or spun and fibrillated fibers that are provided with voids (pores) configured to allow tissue ingrowth into the bio-inert portion 22. The pores are generally larger, on average, than 75 µm.

In one embodiment, the bio-inert portion 22 is a knitted monofilament polypropylene mesh provided as an approximately 225 cm$^2$ mesh having a weight of approximately 21 g/m$^2$ with a pore size of approximately 1121 µm and a thickness of approximately 260 µm. This mesh is thin and light weight (i.e., the basis weight is less than approximately 30 g/m$^2$) to provide a thin and comfortable mesh that is less likely to erode tissue that contacts the mesh and less likely to be sensed through the tissue layers by the patient. Other suitable materials for bio-inert portion 22 include fabrics formed from polyester, polyethylene, silicone, urethanes, polyurethanes, copolymers, or block copolymers of these or suitably similar polymeric materials. Suitable such knitted monofilament polypropylene mesh is available from Coloplast Corp., Minneapolis, Minn. Other suitable woven polypropylene mesh material is available from, for example, HerniaMesh, Chivasso, Italy.

The bio-absorbable portion 24 is attached to the bio-inert portion 22 and includes films that are pre-formed and subsequently attached to the bio-inert portion 22, films that are coated onto or into the bio-inert portion 22, or materials that are molded onto or into the bio-inert portion 22 that are subsequently cured or hardened to support the bio-inert portion 22. In one embodiment, the bio-absorbable portion 24 is formed as a semi-rigid plastic support that is mechanically fixed to the bio-inert portion 22 by the prongs 34. It is desirable that the bio-absorbable portion 24, when formed as a semi-rigid plastic support, be provided with less flexibility than the bio-inert portion 22 to allow the bio-absorbable portion 24 to tension the bio-inert portion 22 and prevents wrinkles on the surfaces 26, 28 of the bio-inert portion 22.

Suitable materials for the bio-absorbable portion 24 include biodegradable polymers, for example, polylactide, polyglycolide, poly(lactide-co-glycolide), or polylactic acid-based polymers. As noted, these bio-absorbable materials are suitably formed into film substrates, coatings, or injection molded supports for the bio-inert portion 22.

In one embodiment, bio-absorbable portion 24 is a molded semi-rigid film superstrate that is disposed across a portion of top surface 28 and coupled to a portion of bottom surface 26 by prongs 34 such that the bio-inert portion 22 is held in tension T. In particular, the prongs 34 displace the corners 36 apart from each other and hold the bio-inert portion 22 in tension T in a manner that prevents wrinkles on the surfaces 26, 28 of the bio-inert portion 22 until tissue grows through the surfaces 26, 28. In one embodiment, the bio-inert portion 22 includes voids 38 or pores 38 that are provided to facilitate tissue ingrowth through and into the bio-inert portion 22.

In one embodiment, the body 30 is provided as an X-shape configured to extend between the corners 36 and cover only a portion of one surface 26 or 28 of the bio-inert portion 22 (e.g., less than an entire surface 26 or 28 of the bio-inert portion 22).

In one embodiment, the bio-inert portion 22 is provided in rectangular form having sides that extend a length L1 between the opposing ends of the bio-inert portion 22, where the ends extent a length L2 between the opposing sides. The X-shape of the body 30 is sized to hold the ends of the bio-inert portion 22 apart by approximately the distance L1 and hold the sides apart by approximately the distance L2. In this manner, the bio-absorbable portion 24 supports the bio-inert portion 22 in a substantially wrinkle-free form that allows tissue ingrowth into the bio-inert portion 22. To this end, the bio-inert portion 22 heals into the implanted location without wrinkles or bulges, which reduces or eliminates the undesirable occurrence of dysparunea in the patient.

Either one or both of the bio-inert portion 22 and the bio-absorbable portion 24 may be coated or treated with an anti-microbial material, or a material that encourages/assists tissue ingrowth.

Figure 3:
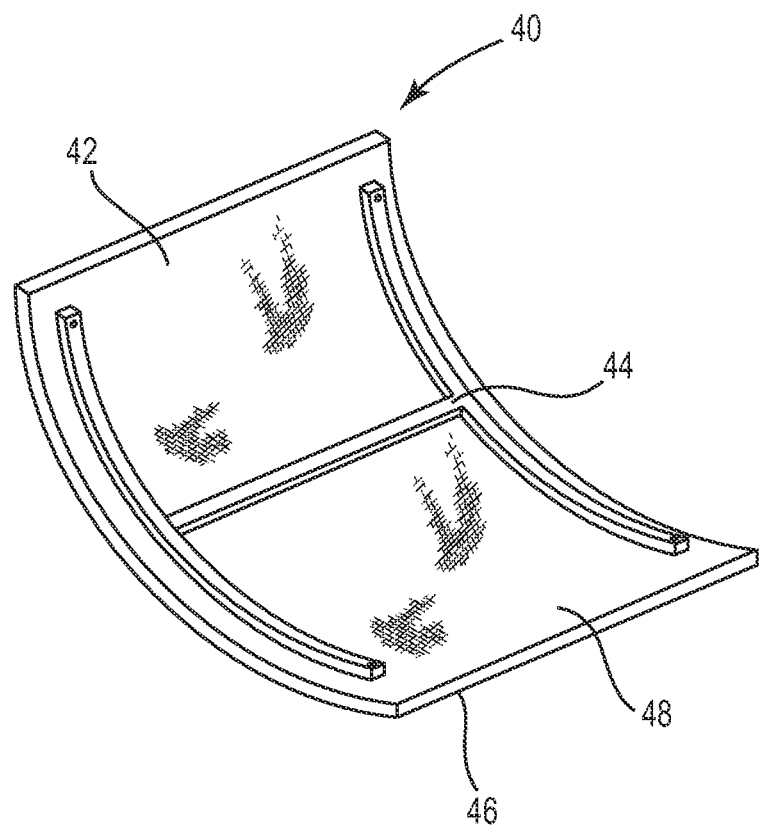
FIG. 3 is a perspective view of another embodiment of an implantable, fabric including a bio-inert portion reinforced by a bio-absorbable portion.
Figure 4:
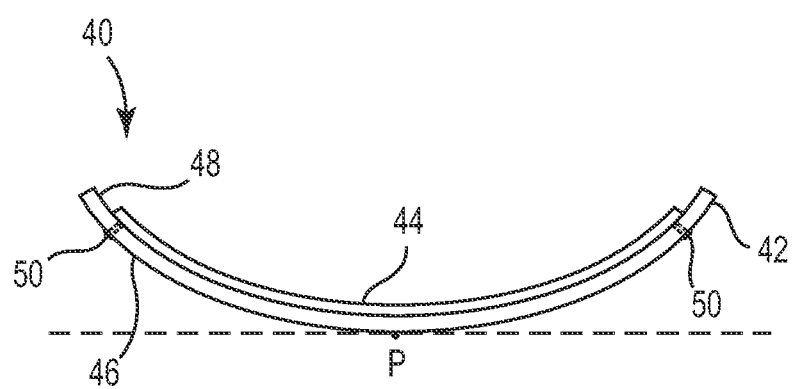
FIG. 4 is a side view of the implantable fabric illustrated in FIG. 3.

FIG. 3 is a perspective view and FIG. 4 is a side view of one embodiment of a body implantable fabric 40. In one embodiment, a body implantable fabric 40 includes a bio-inert portion 42 that is similar to the bio-inert portion 22 described above and a bio-absorbable portion 44 that is configured to support and prevents wrinkles in the bio-inert portion 42 until the body has an opportunity to heal and form tissue ingrowth through the bio-inert portion 42.

In one embodiment, the bio-inert portion 42 includes a first surface 46 opposite a second surface 48, and the bio-absorbable portion 44 is provided as an H-shaped semi-rigid support film that is tacked to the surface 48 by snaps 50. Snaps 50 extend from the first surface 46 through the bio-absorbable portion 44 and attach on the second surface 48. In one embodiment, the bio-absorbable portion 44 and the snaps 50 are both formed from bio-absorbable materials that are similar to those described above for the bio-absorbable portion 24.

In one embodiment, the bio-absorbable portion 44 maintains at least one of the first surface 46 or the second surface 48 of the bio-inert portion 42 in tension such that each of the first and second services 46, 48 are prevented from wrinkling and have at most one point of inflection P. Fabrics that are wrinkled will have more than one point of inflection (for example, at a bottom of each trough and at a top of each ridge). Implantable fabric 40 is supported by the bio-absorbable portion 44 and has at most one point of inflection P and is thus maintained in a substantially wrinkle-free conformation. One of ordinary skill in the art will recognize that a point of inflection is a point along a surface (for example a curved surface) where the slope of a line that is tangent to the surface changes sign.

Figure 5:
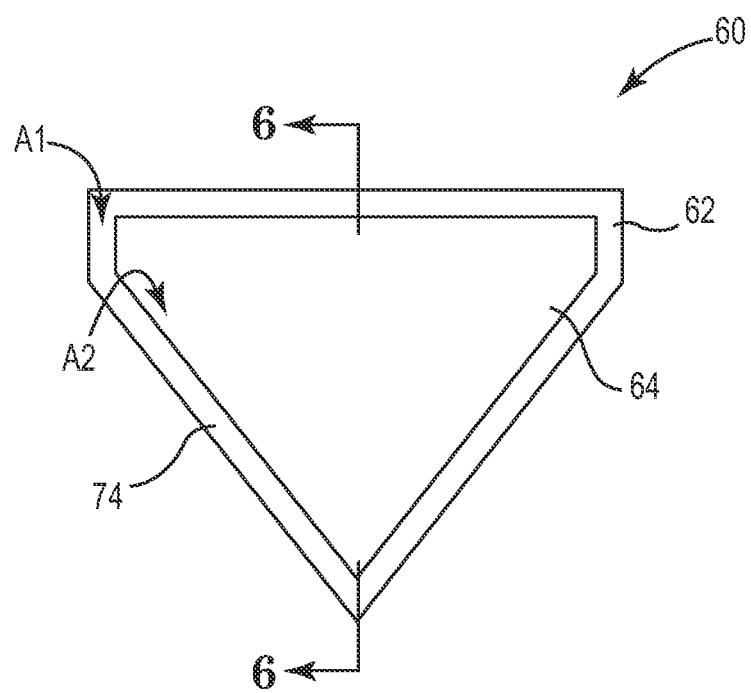
FIG. 5 is a top view of another embodiment of an implantable fabric including a bio-inert portion reinforced by a bio-absorbable portion.
Figure 6:
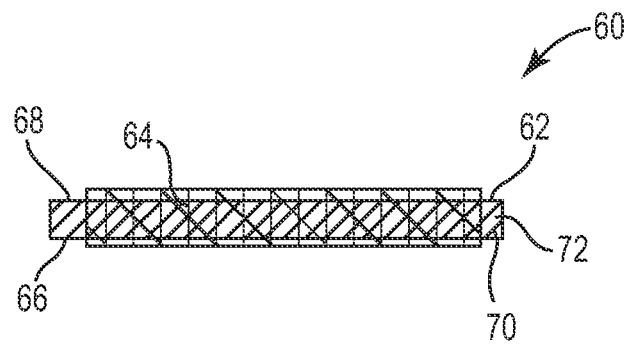
FIG. 6 is a cross-sectional view of the implantable fabric illustrated in FIG. 5.

FIG. 5 is a top view and FIG. 6 is a cross-sectional view of one embodiment of a body implantable fabric 60. In one embodiment, the fabric 60 includes a bio-inert portion 62 supported by a bio-absorbable portion 64. The bio-inert portion 62 includes a first surface 66 opposite a second surface 68, and the bio-absorbable portion 64 is molded or injected or otherwise distributed through the bio-inert portion 62 between the surfaces 66, 68.

In one embodiment, bio-inert portion 62 is provided as an open fabric formed from fibers 70 that are separated by void areas 72, and the bio-absorbable portion 64 is molded through the bio-inert portion 62 around the fibers 70 and into the void areas 72. For example, in one embodiment the bio-inert portion 62 is provided as a mesh of fibers 70 having pores 72 associated with a pore size, and the bio-absorbable portion 64 fills at least some of the pores 72.

In one embodiment, the bio-inert portion 62 has an area A1 and the bio-absorbable portion 64 has an area A2, where the area A2 is less than the area A1. In this regard, the area A1 is larger than the area A2 such that a perimeter 74 of the bio-inert portion 62 is exposed and available for tissue ingrowth after body implantation of fabric 60. Thus, in this embodiment the area of bio-inert portion 62 is larger than the area of the bio-absorbable portion 64. The bio-absorbable portion 64 holds the bio-inert portion 62 under tension in a manner that prevents wrinkles on the surfaces 66, 68 of the bio-inert portion 62 until tissue grows through the surfaces 66, 68.

Suitable processes for attaching the bio-absorbable portion 64 to bio-inert portion 62 include polymer molding, injection molding, transfer molding, or pressing the bio-inert portion 62 between two sandwich layers of the bio-absorbable portion 64. As an example, in one embodiment the bio-inert portion 62 is placed into a mold and the bio-absorbable portion 64 is molded onto the surfaces 66, 68 and through the bio-inert portion 62. Implantation of the fabric 60 into the patient's body results in the bio-absorbable portion 64 eventually breaking down and being absorbed into the body, thus leaving the bio-inert portion 62 in place and substantially wrinkle-free to support tissues of the pelvis without the undesirable effects of dysparunea.

Figure 7:
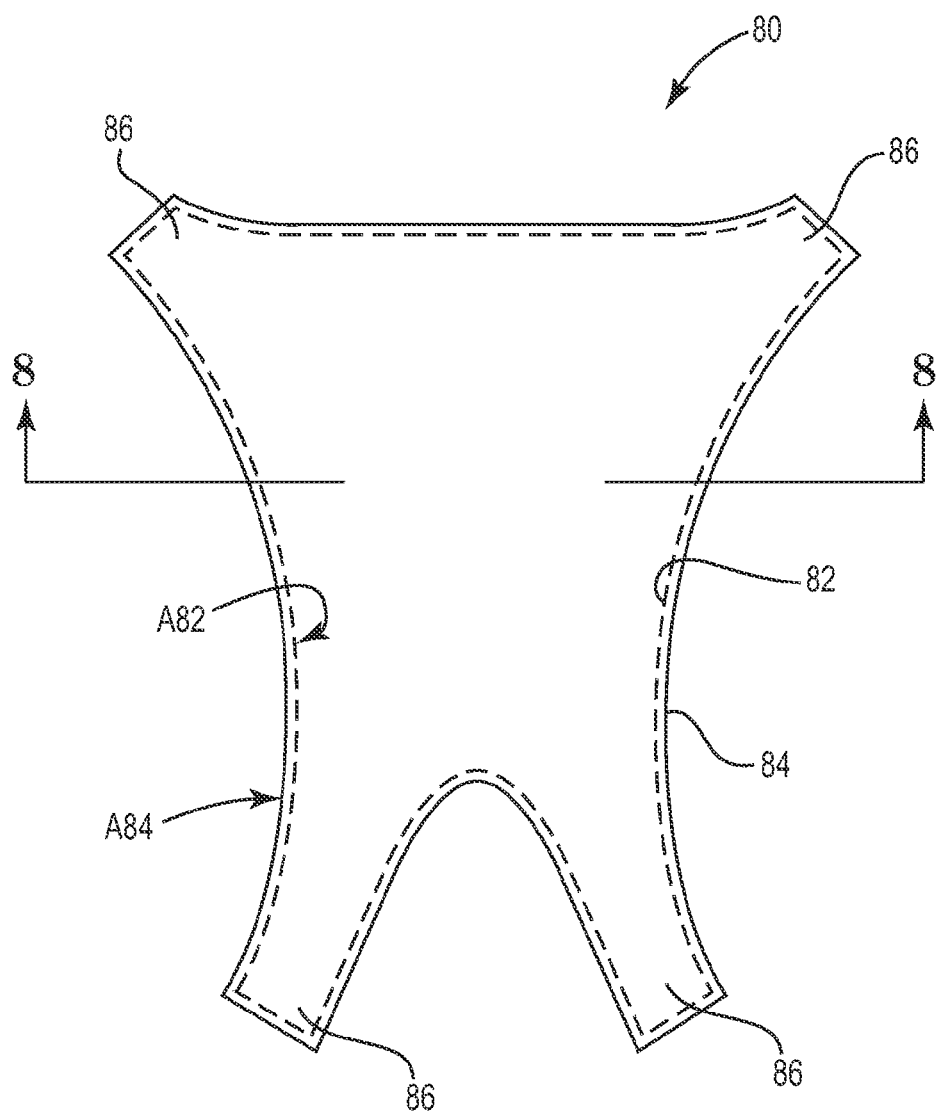
FIG. 7 is a top view of another embodiment of an implantable fabric including a bio-inert portion reinforced by a bio-absorbable portion.
Figure 8:
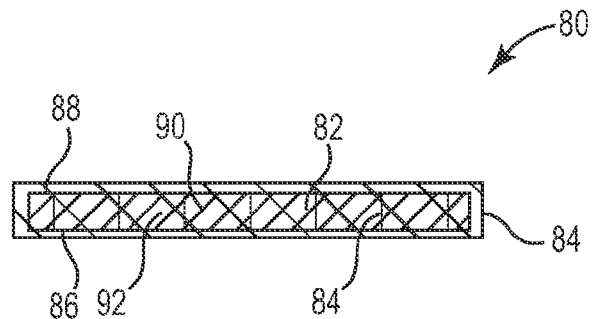
FIG. 8 is a cross-sectional view of implantable fabric illustrated in FIG. 7.

FIG. 7 is a top view and FIG. 8 is a cross-sectional view of one embodiment of a body implantable fabric 80. The fabric 80 includes a bio-inert portion 82 supported and surrounded by a bio-absorbable portion 84. In one embodiment, the bio-inert portion 82 includes a first major surface 86 opposite a second major surface 88, and the bio-absorbable portion 84 is molded through and around the bio-inert portion 82. For example, in one embodiment the bio-inert portion 82 is provided from one of the materials described above for bio-inert portion 22 and includes fibers 90 that are separated by voids 92, and the bio-absorbable portion 84 is molded around the fibers 90 and into substantially all of the voids 92.

In one embodiment, a bio-inert portion 82 is provided as a polygon including arms 86, and the bio-absorbable portion 84 is attached to the polygon and each of the arms 86. In this manner, the bio-inert portion 82 and the arms 86 are extended under tension in a manner that prevents wrinkles on the surfaces 86, 88. In one embodiment, the bio-inert portion 82 has an area A82 and the bio-absorbable portion 84 has an area A84, where the area A84 is greater than the area A82 (i.e., the bio-absorbable portion 84 is molded over the entire bio-inert portion 82).

Figure 9:
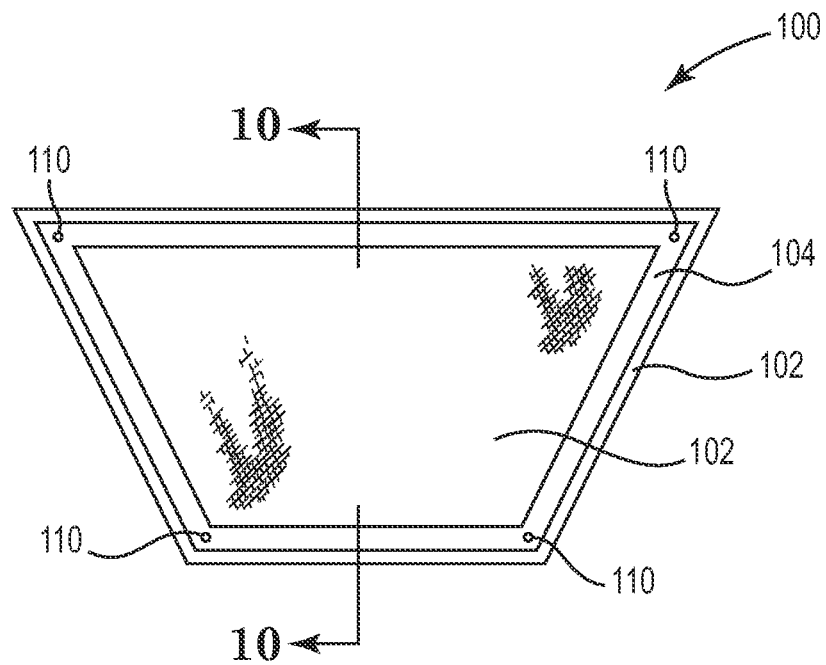
FIG. 9 is a top view of another embodiment of an implantable fabric including a bio-inert portion reinforced by a bio-absorbable portion.
Figure 10:
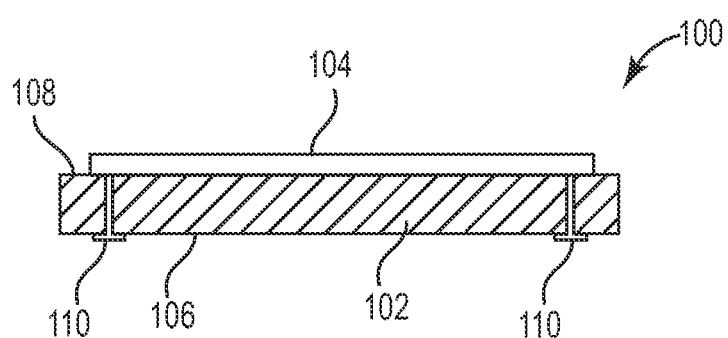
FIG. 10 is a cross-sectional view of the implantable fabric illustrated in FIG. 9.

FIG. 9 is a top view and FIG. 10 is a cross-sectional view of one embodiment of a body implantable fabric 100. Body implantable fabric 100 includes a bio-inert portion 102 and a bio-absorbable portion 104. In one embodiment, the bio-inert portion 102 includes a first major surface 106 opposite a second major surface 108. Each of the first and second surfaces 106, 108 are outwardly exposed such that the first and second surfaces 106, 108 of the bio-inert portion 102 are configured for tissue ingrowth following implantation. The bio-absorbable portion 104 is provided as a frame that is secured to a periphery of one of the surfaces 106, 108 of the bio-inert portion 102 by through-clips 110. The through-clips 110 each include a narrowed body portion that extends and originates from a surface of the bio-absorbable portion 104 and is inserted through the bio-inert portion 102 and a widened end portion configured to retain the bio-inert portion 102.

In one embodiment, the bio-absorbable frame 104 is integrated into the bio-inert portion 102 during fabrication of the fabric 100. In one embodiment, the bio-absorbable frame 104 is provided separately from the bio-inert portion 102 and is configured to be attached to the bio-inert portion 102 by a healthcare worker, for example, prior to body implantation.

In one embodiment, the bio-inert portion 102 is selected from one of the materials described above for the bio-inert portion 22 and the bio-absorbable portion 104 is molded as a semi-rigid frame from one of the materials described above for the bio-absorbable portion 24. The bio-absorbable frame 104 is attached to the periphery of the bio-inert portion 102 by the through-clips 110. It is desirable that the bio-absorbable portion 104 is less flexible than the bio-inert portion 102, and is yet configured to support the bio-inert portion 102 while allowing the bio-inert portion 102 to be rolled or folded or manipulated for implantation into the patient's body. Subsequent to implantation, the bio-absorbable portion 104 is broken down by the body to facilitate tissue ingrowth through the bio-inert portion 102.

FIGS. 11A-11D are schematic illustrations of the implantable fabric 100 prepared for implantation (FIG. 11A) and subsequently implanted into a patient's body Pt (FIGS. 11B-11D) according to one embodiment.

Figure 11A:
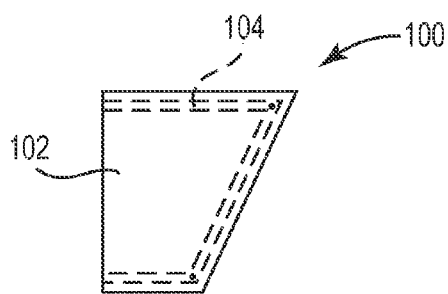
FIGS. 11A-11D are schematic illustrations of the implantable fabric illustrated in FIG. 9 prepared for implantation and subsequently implanted into a patient's body according to one embodiment.

FIG. 11A is a top view of the implantable fabric 100 folded in half to facilitate implantation into a patient. The bio-inert portion 102 has been folded to enclose the bio-absorbable portion 104 between layers of the bio entered portion 102. It is to be understood that the implantable fabric 100 could be rolled or folded multiple times to facilitate implantation into the patient Pt.

Figure 11B:
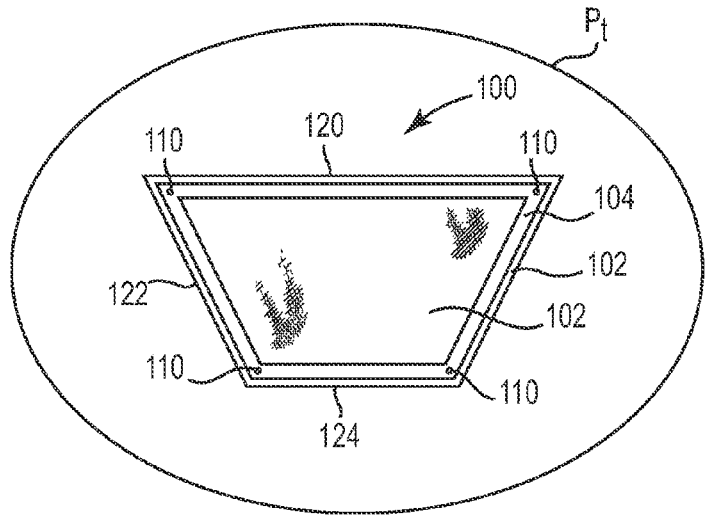
Figure 11C:
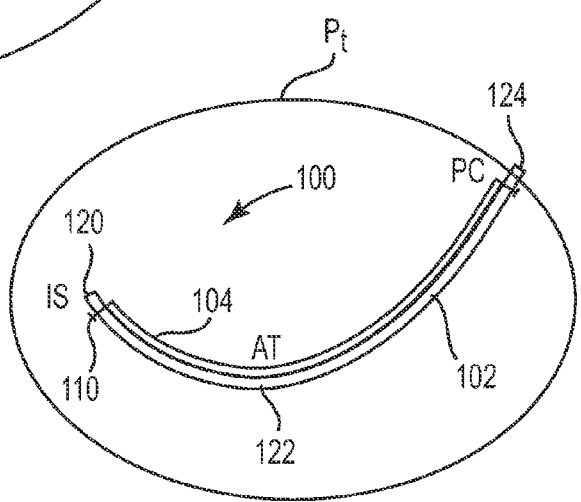

FIG. 11B is a top schematic view and FIG. 11C is a side schematic view of the body implantable fabric 100 implanted into the patient's body Pt. The bio-absorbable portion 104 maintains the bio-inert portion 102 in tension to prevent wrinkles in the top and bottom surfaces of the bio-inert portion 102. The bio-absorbable portion 104 eventually breaks down inside of the patient Pt, leaving the substantially wrinkle-free bio-inert portion 102 implanted inside the patient Pt to support the pelvic tissues.

In one exemplary embodiment, the top end 120 of the fabric 100 is attached to the ischial spine IS, a mid-portion 122 of the fabric 100 is attached to the arcus tendineus AT ligament near the pelvic fascia, and a lower end 124 of the fabric 100 is attached to the pubocervical PC connective tissue. The fabric 100 is thus suspended within the pelvis across the IS, AT, and PC tissues and the frame of the bio-absorbable portion 104 supports and maintains the bio-inert portion 102 to avoid the formation of wrinkles or overlapping areas of the bio-inert portion 102 until tissue ingrowth occurs.

Figure 11D:
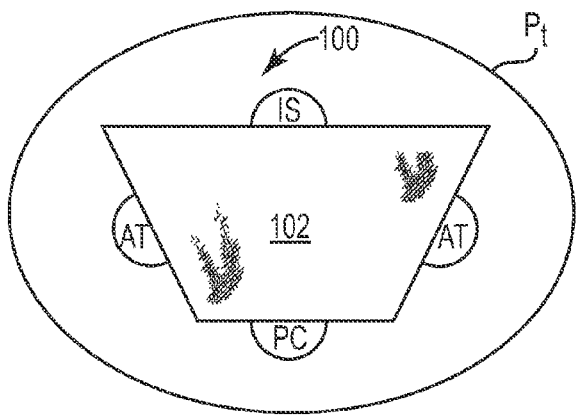

FIG. 11D is a top schematic view of the fabric 100 subsequent to implantation and after healing. The bio-absorbable portion 104 (FIG. 11B) has been broken down by the patient's body Pt leaving the bio-inert portion 102 in place between the IS, AT, and PC tissues. As the bio-absorbable portion 104 is broken down by the body, the patient's tissue grows into the bio-inert portion 102. The bio-absorbable portion 104 prevents wrinkling of the bio-inert portion 102 until tissue ingrowth can occur to fully anchor the fabric 100 into the patient Pt.

With reference to FIGS. 11A-11D, one method of implanting a fabric into a patient's Pt body to repair pelvic organ prolapse includes attaching a bio-absorbable support 104 to the fabric 102, and tensioning the fabric 102 with the bio-absorbable support 104. The bio-absorbable support 104 is attached to the fabric 102 mechanically by snaps or prongs, or by other approaches, such as molding the support 104 over all or some of the fabric 102. Thereafter, the bio-absorbable support 104 and the fabric 102 are implanted into the body Pt and tissue is allowed to grow into opposed major surfaces (106, 108 in FIG. 10) of the fabric 102 to provide a substantially non-wrinkled fabric 102 implanted in the body 104.

A body implantable fabric has been described having a light weight and flexible bio-inert portion that is supported by a bio-absorbable portion, where the bio-absorbable portion prevents wrinkles in the bio-inert portion until tissue ingrowth can occur through the bio-inert portion to anchor it within the patient's body.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable fabric comprising:
    a bio-inert portion having a first surface and an opposing second surface, each of the first and second surfaces being outwardly exposed such that the first and second surfaces of the bio-inert portion are configured for tissue ingrowth prior to and following implantation; and
    a bio-absorbable portion separate from and attachable to the bio-inert portion in a manner that substantially prevents wrinkles on each of the first and second surfaces of the bio-inert portion wherein the bio-absorbable portion is a unitary frame including through-clips extending from a surface of the unitary frame, the through-clips including a body inserted through the bio-inert portion prior to implantation and a widened end portion configured to retain the bio-inert portion.

2. The implantable fabric of claim 1, wherein the bio-inert portion has first and second sides that extend a side length between first and second ends, and the bio-absorbable portion stretches the first end apart from the second end by a distance of approximately the side length.

3. The implantable fabric of claim 2, wherein the first and second ends each extend an end length between the first and second sides, and the bio-absorbable portion stretches the first side apart from the second side by a distance of approximately the end length.

4. The implantable fabric of claim 1, wherein the bio-inert portion defines an area and the bio-absorbable portion is attached to less than an entirety of the area of the bio-inert portion.

5. The implantable fabric of claim 1, wherein the bio-absorbable portion comprises a film that is mechanically attached to one of the first and second surfaces of the bio-inert portion.

6. The implantable fabric of claim 1, wherein the unitary frame is attached to a periphery of either the first or second surface of the bio-inert portion.

7. The body implantable fabric of claim 1, wherein the through-clips include a narrowed body that extends from the surface of the unitary frame member.

8. The body implantable fabric of claim 1, wherein the body is integrally formed with the bio-absorbable portion.

9. A body implantable fabric comprising:
    a porous bio-inert portion having opposed, outwardly exposed major surfaces, such that the bio-inert portion is configured for tissue ingrowth into the bio-inert portion through the opposed, outwardly exposed major surfaces prior to and following implantation;
    a bio-absorbable portion provided as a unitary frame including through-clips extending from a surface of the unitary frame; and
    wherein the through-clips each include a body portion and a widened end portion and are attached to the porous bio-inert portion by receiving the body portion through the bio-inert portion prior to implantation and provided to allow a healthcare worker to attach the bio-absorbable portion to the porous bio-inert portion prior to implantation;
    wherein the bio-absorbable portion applies tension to the porous bio-inert portion to prevent formation of wrinkles in the porous bio-inert portion.

10. The body implantable fabric of claim 9, wherein the bio-absorbable portion is configured to allow the porous bio-inert portion to be folded for implantation.

11. The body implantable fabric of claim 9, wherein the porous bio-inert portion comprises a first major surface opposite a second major surface, each of the major surfaces configured for tissue ingrowth.

12. The body implantable fabric of claim 9, wherein the unitary frame is attached to a periphery of a major surface of the bio-inert portion.

13. The body implantable fabric of claim 9, wherein the through-clips include a narrowed body that originates from the surface of the unitary frame member.

14. The body implantable fabric of claim 9, wherein the body portion is integrally formed with the bio-absorbable portion.

* * * * *